US008689976B2

(12) United States Patent
Wittrock

(10) Patent No.: US 8,689,976 B2
(45) Date of Patent: Apr. 8, 2014

(54) STERILIZABLE POUCH FOR MEDICAL INSTRUMENTS

(75) Inventor: Paul Wittrock, Newbury Park, CA (US)

(73) Assignee: Dux Industries, Inc., Oxnard, CA (US)

( * ) Notice: Subject to any disclaimer, the term of this patent is extended or adjusted under 35 U.S.C. 154(b) by 226 days.

(21) Appl. No.: 12/983,609

(22) Filed: Jan. 3, 2011

(65) Prior Publication Data

US 2012/0168334 A1   Jul. 5, 2012

(51) Int. Cl.
*B65D 75/30* (2006.01)
*B65D 33/18* (2006.01)

(52) U.S. Cl.
USPC ............... 206/459.1; 206/459.5; 206/484

(58) Field of Classification Search
USPC ........ 206/459.5, 459.1, 484, 438, 363; 383/5, 383/211, 200
See application file for complete search history.

(56) References Cited

U.S. PATENT DOCUMENTS

| | | | |
|---|---|---|---|
| 3,325,084 A * | 6/1967 | Ausnit | 229/77 |
| 3,685,720 A | 8/1972 | Brady | |
| 3,692,233 A * | 9/1972 | Carter, Jr. | 229/71 |
| 3,768,725 A | 10/1973 | Pilaro | |
| 3,819,106 A * | 6/1974 | Schuster | 206/439 |
| 4,194,622 A * | 3/1980 | Lewis | 206/363 |
| 4,502,599 A * | 3/1985 | Perecman | 206/554 |
| 4,937,040 A * | 6/1990 | Holcomb et al. | 383/5 |
| 5,056,930 A * | 10/1991 | Mestetsky | 383/5 |
| 5,071,061 A * | 12/1991 | Willis | 229/303 |
| 5,344,017 A | 9/1994 | Wittrock | |
| 5,832,145 A * | 11/1998 | Dais et al. | 383/211 |
| 5,922,428 A | 7/1999 | Pufahl | |
| 6,149,302 A * | 11/2000 | Taheri | 383/5 |
| 6,189,694 B1 | 2/2001 | Weiss et al. | |
| 6,969,197 B2 | 11/2005 | Sedley | |
| 7,743,915 B2 * | 6/2010 | Murphy | 206/273 |
| 2003/0081864 A1 * | 5/2003 | Baker et al. | 383/204 |
| 2010/0094238 A1 * | 4/2010 | Scarano | 604/385.13 |

OTHER PUBLICATIONS

International Search Report from corresponding PCT Application, PCT/US2011/000017. dated Sep. 30, 2011.

* cited by examiner

*Primary Examiner* — Steven A. Reynolds
(74) *Attorney, Agent, or Firm* — Koppel, Patrick, Heybl & Philpott; Michael J. Ram

(57) ABSTRACT

An improved sealable pouch has an interior volume for receiving products for sterilization and an integral, foldable flap sealable to the pouch to provide a fully enclosed interior volume. Included on one or more portions of the pouch are indicia, preferably at least a first and second spaced apart indicia, to aid in proper folding of the flap. The indicia provide alignment means so that when the flap is properly folded to provide a leak proof seal, a predetermined portion of the indicia is covered by the flap. An improper seal can be visually determined to exist if all of the indicia or none of the indicia is visible after the seal is made. A proper seal is evidenced by only a portion of the first and second indicia being covered by the flap.

10 Claims, 7 Drawing Sheets

STERILIZABLE POUCH FOR MEDICAL INSTRUMENTS

It is well known to provide a pouch for receiving medical instruments for sterilization. Such pouches are typically formed from two films of material which are non-porous or are sufficiently porous to allow sterilants, such as ethylene oxide or steam to penetrate the film while excluding contaminants from entering the pouch once the contents are sterilized. The pouch materials may also be chosen so they are stable under radiation sterilization conditions. Typically one surface of the pouch is composed of a fibrous material, such as paper or TYVEK. This porous material is heat sealed along three edges to a transparent plastic film, such as polyester, high density polyethylene, polypropylene, etc. A fourth edge is left open to allow insertion of a clean but not yet sterilized instrument into the pouch. The fourth edge may then be heat sealed to form a closed pouch with the instrument in the 3 dimensional area within the sealed edges. An alternative is to provide, at the fourth edge a portion of one of the films, for example the porous material (the rear film), extending beyond the top edge of the front film to form a flap. The flap has an adhesive material applied to the upward face of that film so that when the flap is properly folded and placed on the upper surface of the front film, the two films are adhesively secured together in an airtight manner. To fully seal the pouch it is extremely important that the fold of the flap be properly accomplished. If not properly done a complete seal will not be formed and an access point will be provided for entry of contaminants into the pouch. However, it can be difficult to ascertain if this fold has been improperly made and as a result the pouch is not fully sealed.

SUMMARY

A pouch for receiving instruments for sterilization comprising an enclosed space with one open end, a flap extending from that open end, the flap having an adhesive covering a face of the flap, the adhesive being positioned for sealing the open end when folded. Proper folding and sealing is evidenced by the flap end being located between positioning marks on the face of the pouch.

DETAILED DISCUSSION

Figure 1:
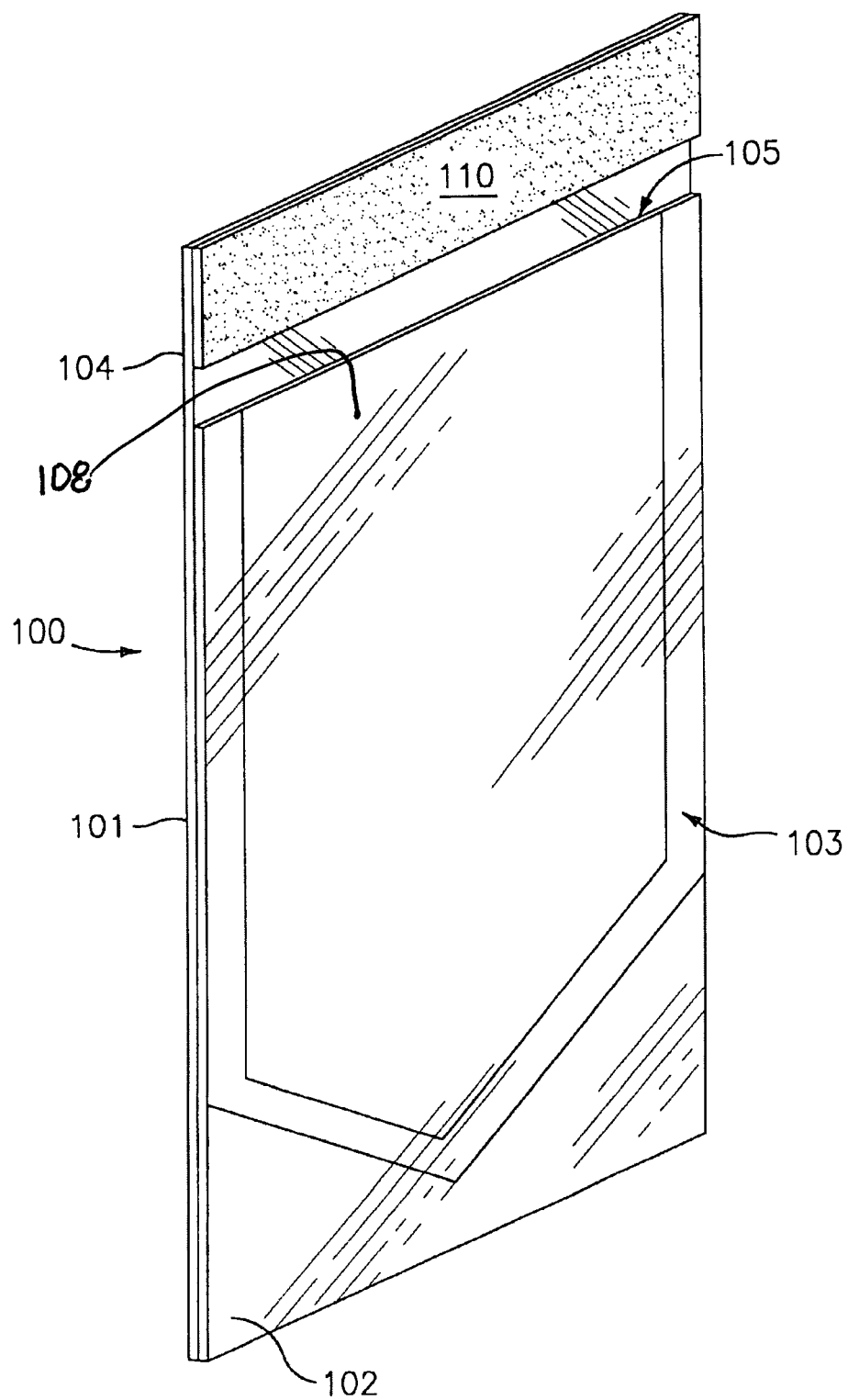
FIG. 1 is a perspective view of a first example of a prior art pouch.
Figure 2:
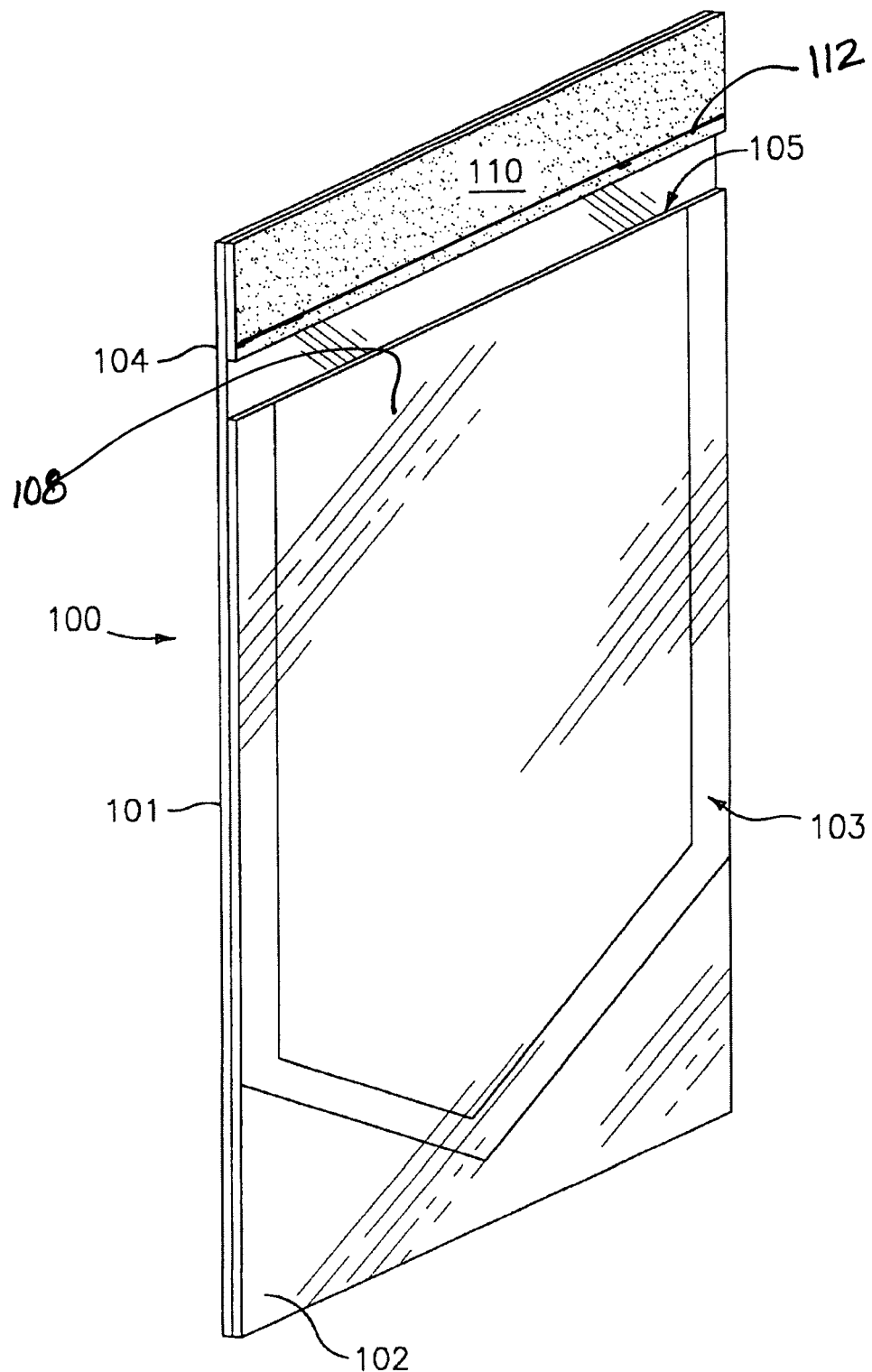
FIG. 2 is a second example of a prior art pouch having a folding line to assist in proper folding of the flap.

FIGS. 1 and 2 show examples of prior art pouches used for storing instruments for sterilization. The pouch 100 comprises a first film 101 with a second film 102 placed on top thereof, the first and second films 101, 102 adhered together by an air tight seal 103, typically a heat seal, along three edges (the left side, right side and bottom). The top edge 105 of the second film is not sealed to the first film so a product can be place into the internal space 108 formed by sealing the other three sides together. The first film has a flap 104 extending above the top 105 of the first film 102. A pressure sensitive adhesive 110 is applied to at least a portion of the flap, that adhesive 110 usually extending across the entire width of the flap 104. A release paper, not shown, is usually placed over the adhesive area to protect the adhesive until it is used to adhesively form a closed space in the pouch 100. Alternatively, a contact adhesive may be used with a first adhesive film applied to the flap 104 and a second compatible adhesive applied to the second film 102. However, the particular adhesive used to seal the pouch is not limited to the described embodiments and one skilled in the art can substitute various other adhesive systems or securing means for attaching the folded flap to the pouch surfaces.

FIG. 2 is the same as FIG. 1 except for the addition of a fold line 112 which may be printed on the inner surface, as shown, the outer surface (not shown) or both surfaces of the flap 104 to guide the user in making a proper fold of the flap to seal the pouch. Alternatively, the fold line 101 can be in the form of a perforation in the flap 104, a preformed fold or various other indicia to aid in making a proper fold.

Figure 3:
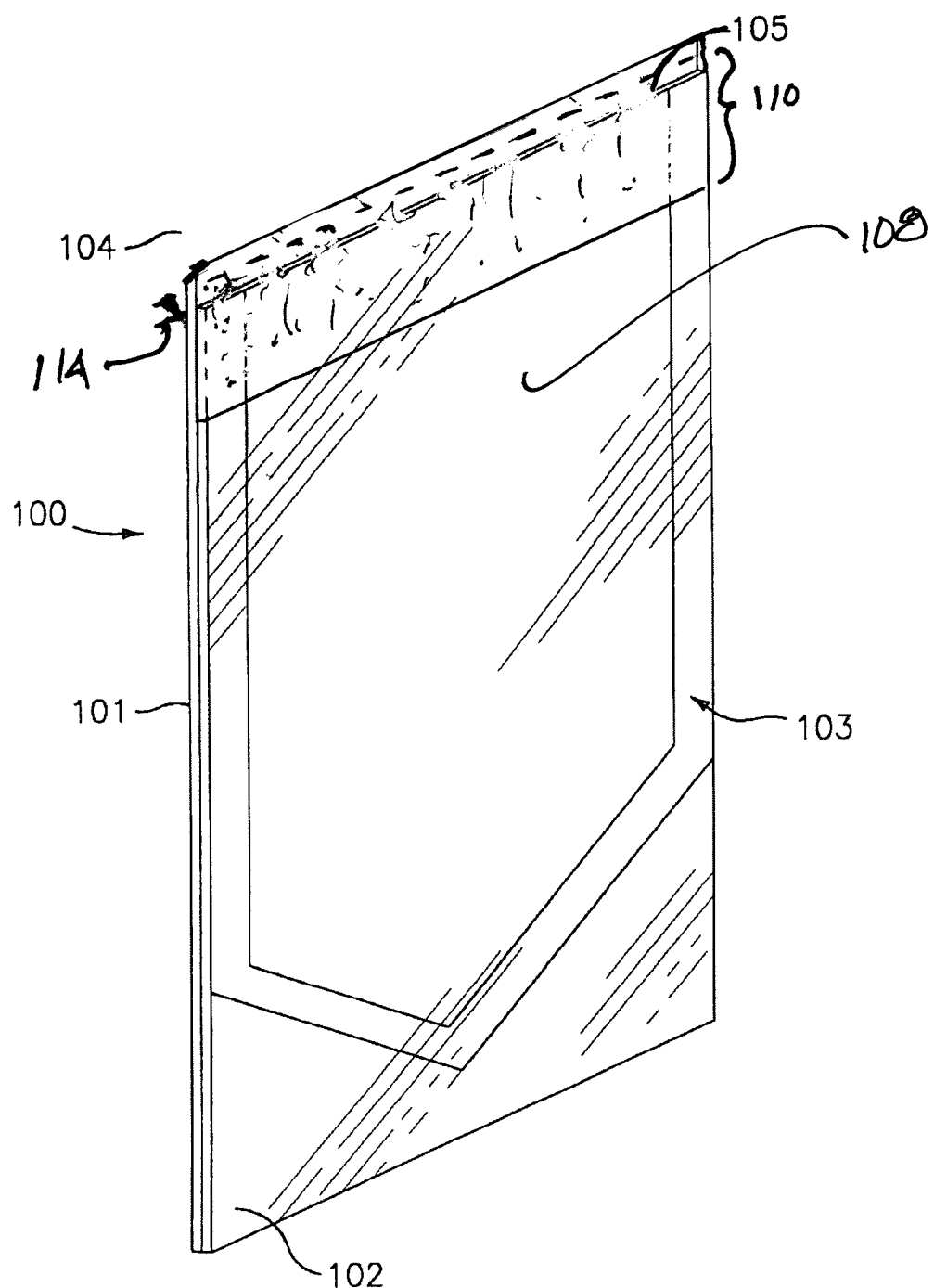
FIG. 3 shows a proper fold of the pouch of FIG. 1 or 2.
Figure 4:
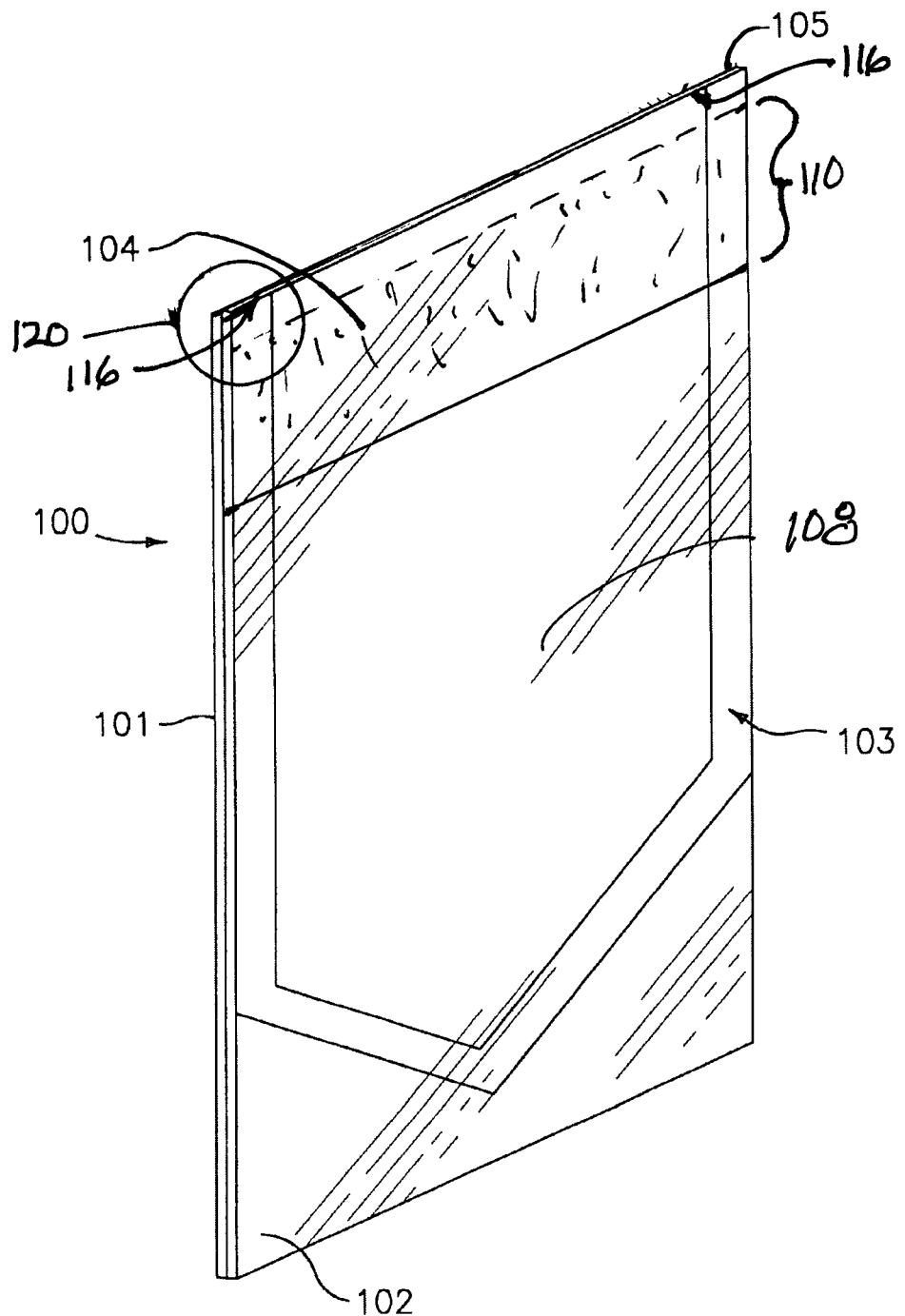
FIG. 4 shows an improper fold of the pouch of FIG. 1 or 2.

FIG. 3 shows the pouch 100 of FIG. 1 or 2 with the flap 104 folded to form a proper seal. In a preferred embodiment once the flap is folded half of the adhesive adheres to the lower portion of the flap 104 portion of the first film 101 and half of the adhesive adheres to the surface of the second film 102. For clarity in visualizing the proper seal, the adhesive portion 110, which is now hidden, is shown. The adhesive 110 on the flap 104 is now attached to and fully covers an upper portion of the second film 102, the opening 105 at the top of the second film 102 and the adjacent portion 114 of the flap 104, thus forming a proper seal. However, a proper fold and seal is not always obtained and often it is difficult to ascertain if a proper seal is made. For example, the flap may not be folded along the fold line 112 or the fold may be at a slight angle to the fold line. Sometimes these faulty folds may be acceptable. However, in other instances there may be too great an error and the sealed pouch has an air gap. For example, a common error is to fold the pouch along the second film top edge 105. Another common error occurs when the item in the pouch is small. The user folds the pouch to the smallest possible size such that the adhesive portion is somewhere along the length of the second film. In each instance, the adhesive 110 only attaches to the second film 102 and an opening 116 is then left at the top left and right of the pouch. As a result, air can unintentionally enter the not fully enclosed internal space 108 such as in FIG. 4 in which the fold is made along the second film top edge 105 is shown.

Figure 8:
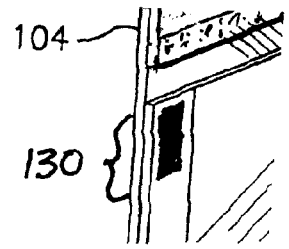
FIGS. 8-11 are partial views of the pouch of FIG. 6 show representative alternative designs for the seal indicator.
Figure 5:
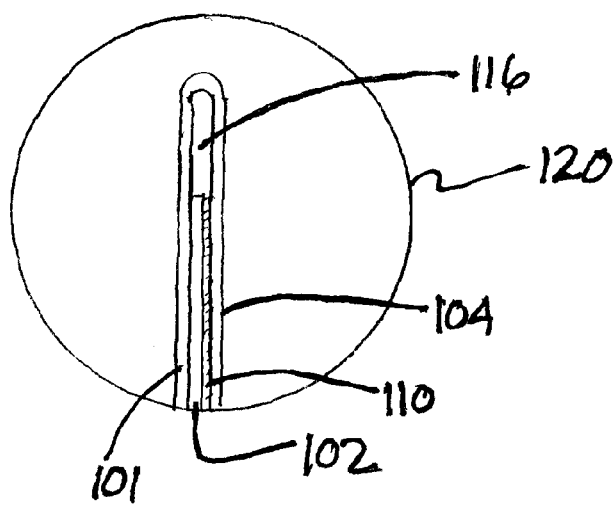
FIG. 5 is an enlarged side view of an improper seal within the area of circle 120 of FIG. 4.
Figure 9:
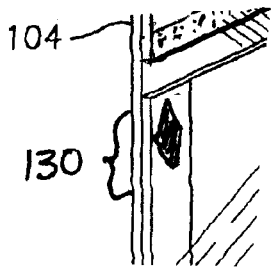
Figure 10:
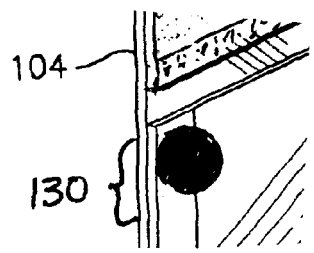
Figure 11:
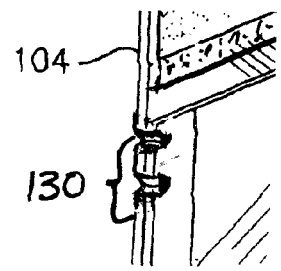
Figure 6:
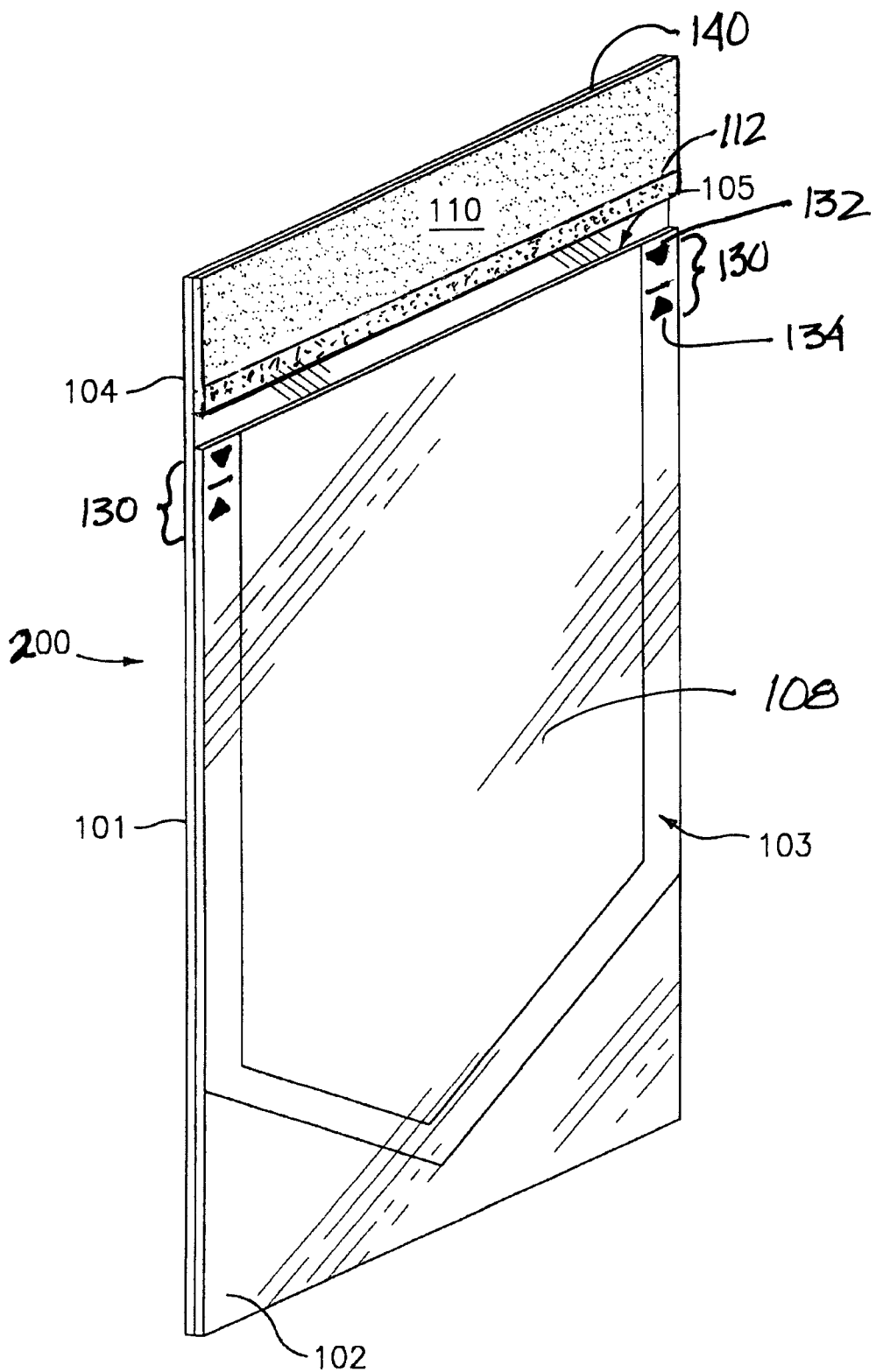
FIG. 6 is a perspective view of a pouch incorporating features of the present invention which allow for a quick visual verification of a proper fold resulting in a full seal.
Figure 7:
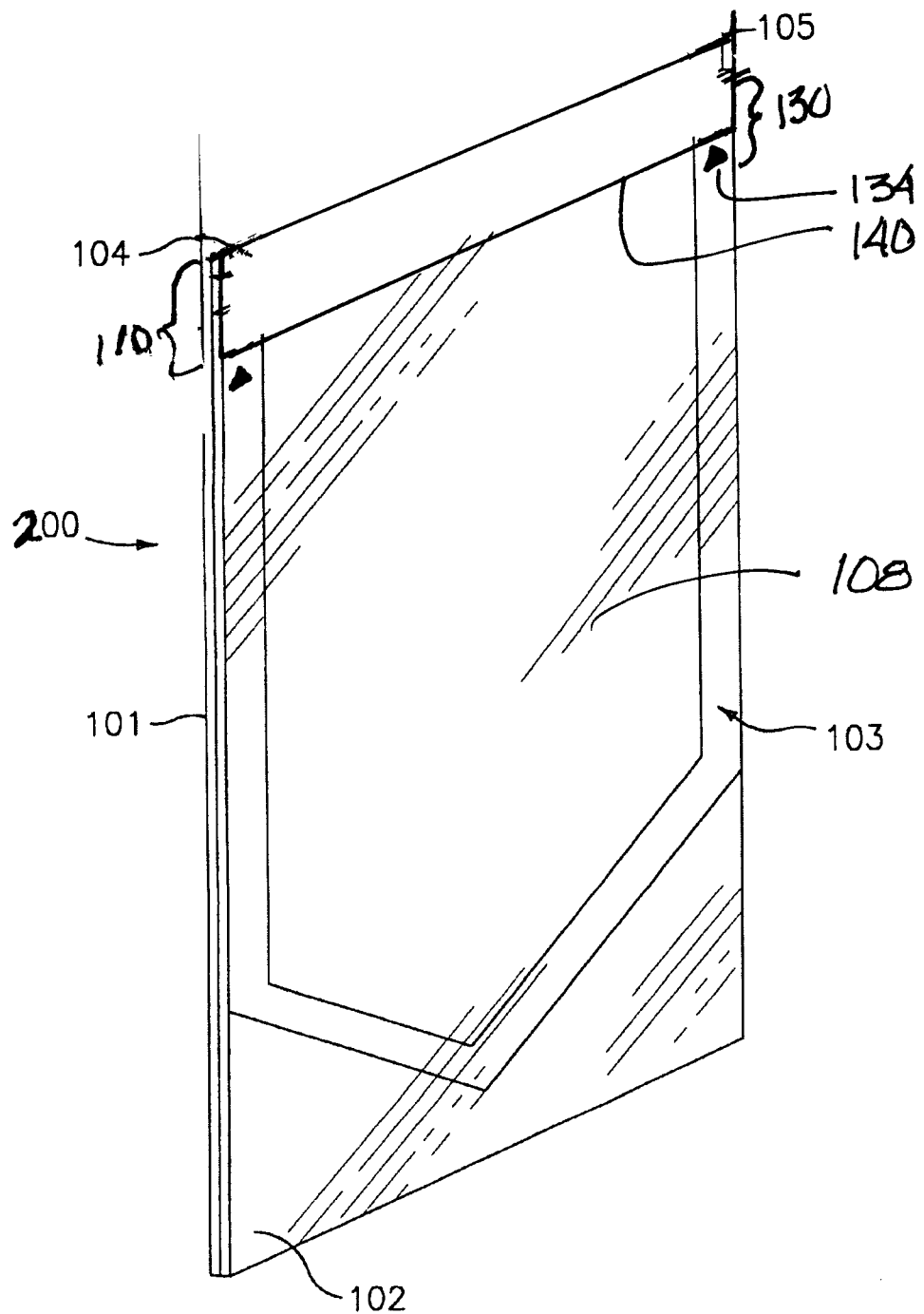
FIG. 7 shows a pouch incorporating features of the invention with properly folded flap.

FIG. 6 illustrates an embodiment of a pouch 200 which includes a guide portion 130 to insure proper closure. The features of the prior art pouches described above are present in the pouch 200. It may or may not include a fold line 112. FIGS. 6 and 7 show a first embodiment of the guide portion 130 utilizing printed symbols. FIGS. 8-10 show alternative printed symbols. As a further alternative, instead of printing the symbols they can be punched through, die cut through the sealed edge of the pouch, or embossed into the pouch. As a still further alternative, FIG. 11 shows notches cut into the edge of the pouch. The guide portion 130 has two functions. First, it provides a folding guide. As long as the top edge 140 of the flap is between the top 132 and bottom 134 of the guide portion 130 a proper seal is obtained. The distance between top edge 132 and the bottom edge 134 is predetermined by the manufacturer based on the pouch, flap and adhesive area dimensions. Secondly, once the pouch is sealed an observer can readily determine if a proper seal is obtained. On observing the sealed flap, if the entirety of, or none of, either of the left or right guide portion 130 is visible then the seal is not proper and a leak most likely exists. However, if the flap 104 covers a portion of both of the left and right guide portions 130, a proper seal is obtained.

The guide portions 130 are show in FIGS. 6-11 as left and right indicia at the left and right edges of the pouch. However one skilled in the art will recognize that the indicia may be any manner of marks across the face of the pouch for alignment of the top end 140 of the flap. Further, there is no limitation as to the shape of the guide portions 130 or the manner of applying the guide portion 130 to the pouch. FIGS. 8-11 providing four different alternatives given as examples and not as limitations on the scope of the invention disclosed herein.

I claim:

1. An improved peel-open pouch for sterilized articles, said pouch having first and second films comprising a front wall and a rear wall, said front and rear walls being heat-sealed to each other along two side edges and a bottom edge thereof,
   a fourth edge having a sealable inlet, the rear wall at the fourth edge having a flap extending beyond the front wall at the fourth edge, the flap being bendable to overlap the front wall adjacent the fourth end, the flap having an adhesive material on a surface thereof such that when the flap overlaps the front wall and adjacent rear wall portion, the flap is adhesively secured to the front wall and said adjacent portion to form a fully enclosed space within the pouch,
   the improvement comprising at least first and second indicia spaced apart across the width of the peel-open pouch providing alignment means for positioning a rear wall fourth edge at and covering a portion of both of said first and second indicia upon bending of the flap
   wherein each of the first and second indicia spaced apart across the width of the peel-open pouch for providing alignment means comprise a first pair of alignment marks adjacent one of the two side edges and longitudinally spaced apart and a second pair of alignment marks adjacent the other of the two side edges and longitudinally spaced apart such that when said flap is adhered to the front wall to form the fully enclosed space within the pouch only one of each pair of alignment marks is covered by the flap.

2. The improved peel-open pouch of claim 1 wherein the first and second spaced apart pairs of indicia comprising left and right indicia spaced laterally across the width of the pouch provide pairs of alignment points for positioning the edge of the folded flap.

3. The improved peel-open pouch of claim 2 wherein formation of the fully enclosed space within the pouch is evidenced by only a portion of the left and right pairs of indicia being covered by the flap after folding.

4. The improved peel-open pouch of claim 1 wherein the indicia are printed on the front wall, or on the rear wall visible through the front wall.

5. The improved peel-open pouch of claim 1 wherein the indicia comprises cut symbols, symbols piercing the first and second film or indicia embossed onto the film.

6. An improved method of assuring a complete seal of a pouch used for sterilization of items placed therein wherein the pouch has first and second films comprising a front wall and a rear wall, said front and rear walls being heat-sealed to each other along two side edges and a bottom edge thereof and a fourth edge having a sealable inlet, the rear wall at the fourth edge having a flap extending beyond the front wall at the fourth edge, the flap being foldable to overlap the front wall adjacent the fourth end, the flap having a sealing material on a surface thereof, such that when the flap is folded to overlap the front wall and adjacent rear wall portion, the flap being secured to the front wall and said adjacent portion to form a fully enclosed space within the pouch,
   the improvement comprising providing at least a first and second indicia spaced apart across the width of the peel-open pouch, said indicia providing alignment means for positioning an edge of a rear wall in alignment with a portion of said first and second indicia upon bending of the flap
   the first and second indicia comprising a first pair of alignment marks adjacent a first of the two side edges and longitudinally spaced apart along the edge and a second pair of alignment marks adjacent a second of the two side edges and longitudinally spaced along the edge, such that when said flap is adhered to the front wall formation of the fully enclosed space within the pouch is evidenced by only one of the pair of each of the alignment marks comprising the indicia at the first and second side edges being covered by the flap.

7. The improved method of claim 6 wherein the indicia comprising left and right indicia spaced laterally across the width of the pouch provide alignment points for positioning the edge of the folded flap.

8. The improved method of claim 7 wherein formation of the fully enclosed space within the pouch is evidenced by only a portion of the left and right pair of indicia is covered by the flap after folding.

9. The improved method of claim 6 wherein the indicia is printed on the front wall, or on the rear wall visible through the front wall.

10. The improved method of claim 6 wherein the indicia comprise cut symbols, symbols piercing the first and second film or indicia embossed onto the film.

* * * * *